United States Patent [19]

Kriesel

[11] Patent Number: 5,263,940

[45] Date of Patent: Nov. 23, 1993

[54] FLUID DISPENSER

[75] Inventor: Marshall S. Kriesel, Saint Paul, Minn.

[73] Assignee: Science Incorporated, Bloomington, Minn.

[21] Appl. No.: 870,521

[22] Filed: Apr. 17, 1992

[51] Int. Cl.⁵ .......................................... A61M 37/00
[52] U.S. Cl. ...................................................... 604/132
[58] Field of Search ............. 604/132, 131, 93, 82-85, 604/92; 128/DIG. 12

[56] References Cited

U.S. PATENT DOCUMENTS

| 3,468,308 | 9/1969 | Bierman | 604/132 X |
| 3,469,578 | 9/1969 | Bierman | 604/246 X |
| 4,386,929 | 6/1983 | Perry et al. | |
| 4,419,096 | 12/1983 | Leeper et al. | |
| 4,915,693 | 4/1990 | Hessel | |
| 4,994,031 | 2/1991 | Theeuwes | 604/85 |
| 5,122,116 | 6/1992 | Kriesel | 604/132 X |

FOREIGN PATENT DOCUMENTS

464761A1 8/1992 European Pat. Off. .

Primary Examiner—Gene Mancene
Assistant Examiner—Jeffrey A. Smith
Attorney, Agent, or Firm—J. E. Brunton

[57] ABSTRACT

An elastomeric bladder type infusion device for delivering a beneficial agent, such as a drug to a patient at substantially a constant rate. The device uniquely includes an internally disposed functional substrate which carries the beneficial agent so that it can be mixed with the fluid as the fluid is being introduced into the device to distend the bladder to make it an energy source for controllably dispensing the solution mixture to a patient.

18 Claims, 3 Drawing Sheets

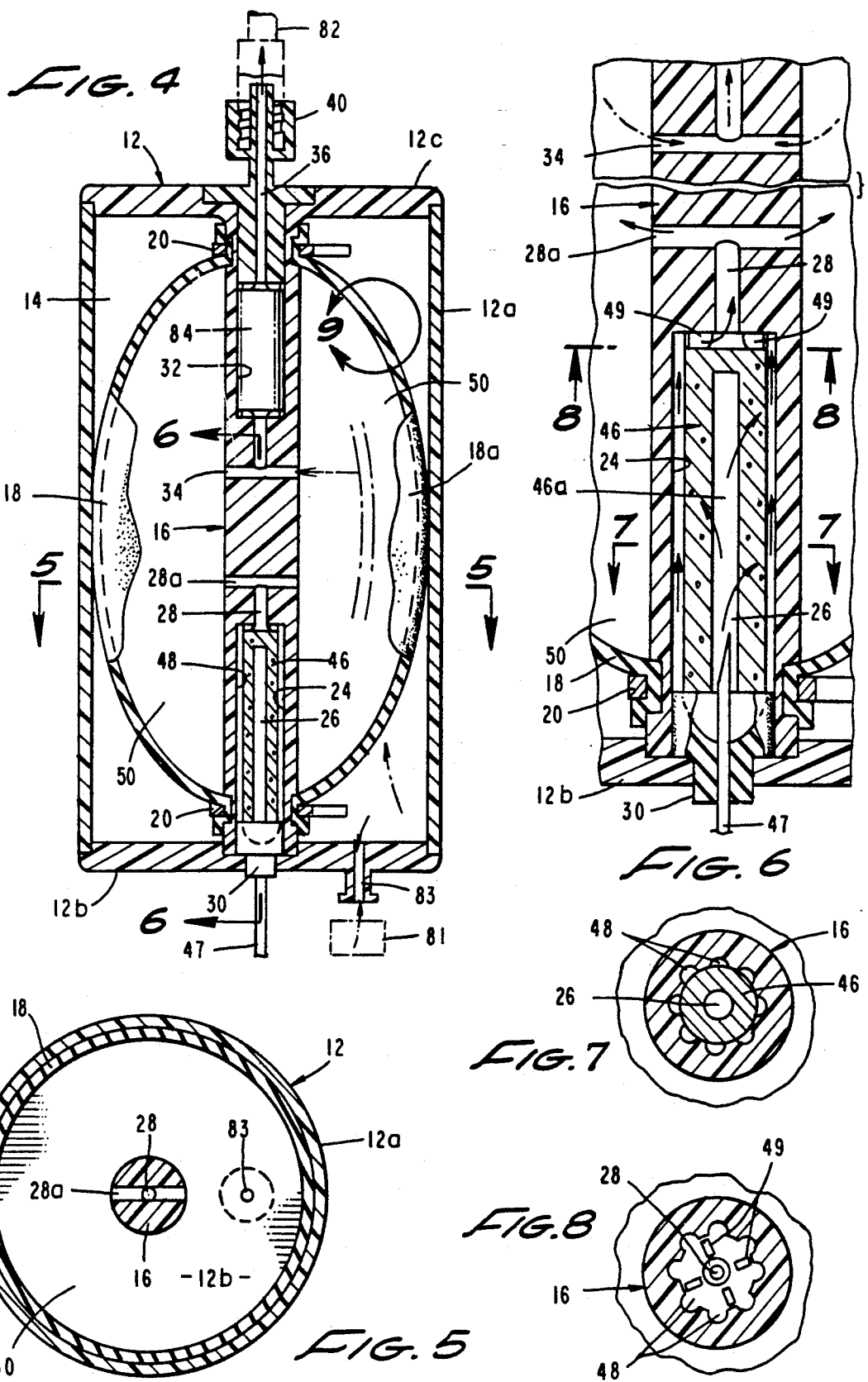

FLUID DISPENSER

BACKGROUND OF THE INVENTION

1. Field of the Invention

The present invention relates generally to infusion devices. More particularly, the invention concerns an elastomeric bladder type infusion device which is used for delivering a beneficial agent to a patient at a substantially constant rate. The device uniquely includes means for intermixing a first compound, such as a drug, with a second component such as a parenteral liquid prior to delivering the solution thus formed to the patient.

2. DISCUSSION OF THE INVENTION

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided on the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. The Hessel device also includes a one-way valve on the stress member which permits flow in the influent lumen only in the direction of the interior of the bladder.

Another type of balloon type infusion device is disclosed in U.S. Pat. No. 4,386,929 issued to Perry, et al. The Perry, et al. device has spaced apart inlet and outlet means and the bladder which is capable of expanding and contracting radially and axially upon inflation and deflation. When deflated the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated, before its subsequent inflation and deflation, substantially complete expulsion of the fluid contents of the bladder can be obtained.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time. In the device described in U.S. Pat. No. 3,469,578, the liquid is expelled solely by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tube-like member which is typically distendable both lengthwise and laterally when initially pressured. Admission and discharge of liquid is of necessity, through a single neck, or outlet portion of the balloon-like bladder.

None of the prior art devices known to applicant have the unique capability of the present invention for internally mixing a first compound, such as a drug, with a second compound such as a diluent, prior to expelling the beneficial agent thus formed from the device.

SUMMARY OF THE INVENTION

It is an object of the present invention to provide an elastomeric bladder stored energy type infusion device which can be filled with a fluid such as a diluent and which during filling efficiently mixes the diluent with an additive such as a drug or other type of beneficial agent.

More particularly, it is an object of the invention to provide an infusion device of the aforementioned character which provides the opportunity to add to the diluent or other parenteral fluid being introduced into the device selected elements, chemical compounds and biologically active materials such as drugs, medicaments, biological agents, or other therapeutic agents (additives). This addition is accomplished by removably affixing the selected additives to various forms of support structures which can be placed within the path of the fluid flowing through the device. In this way, the delivery system of the invention can be safely rendered therapeutically active upon hydration of the additive with the selected parenteral fluid.

Another object of the invention is to provide an elastomeric bladder type infusion device of the class described in which make-up air can be added during the fluid delivery operation to insure that a uniform expelling of the fluid can be realized.

Another object of the invention is to provide a device of the character described in the preceding paragraphs in which a large number of additives can be selectively mixed at controlled rates with the filling fluid.

Still another object of the invention is to provide a device of the class described which includes internally disposed flow control means for precisely controlling the rate of flow of the fluid from the device.

Another object of the invention is to provide a bladder type infusion-mixing device in which the beneficial agent to be added to the filling fluid is removably affixed to supporting substrates of various materials and configuration.

Yet another object of the invention is to provide a device of the character described in the preceding paragraphs which is highly reliable inexpensive to produce in quantity, easy to use and readily disposible after use.

BRIEF DESCRIPTION OF THE DRAWINGS

FIG. 1.

FIG. 4 is a cross-sectional view similar to FIG. 2 but showing the bladder assembly of this form of the invention in a distended position.

FIG. 5 is a cross-sectional view taken along lines 5—5 of FIG. 4.

FIG. 6 is an enlarged fragmentary, cross-sectional view taken along lines 6—6 of FIG. 4.

FIG. 7 is a cross-sectional view taken along lines 7—7 of FIG. 6.

FIG. 8 is a cross-sectional view taken along lines 8—8 of FIG. 6.

DESCRIPTION OF ONE FORM OF THE INVENTION

Figure 1:
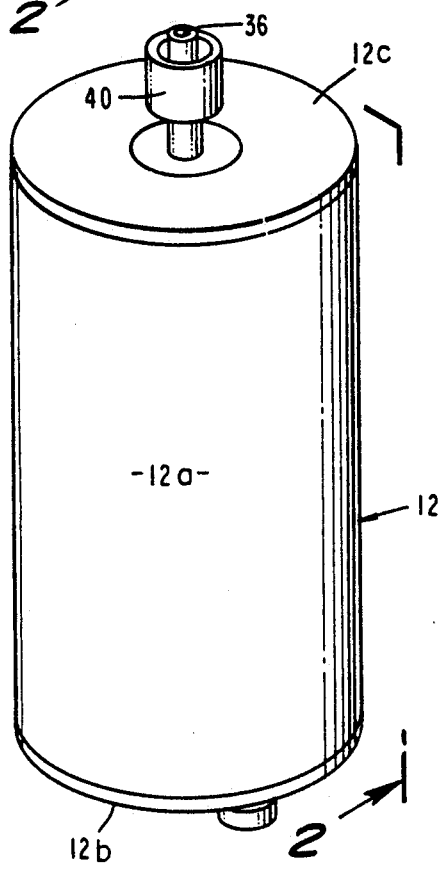
FIG. 1 is a generally perspective view of the fluid delivery device of one form of the present invention.
Figure 2:
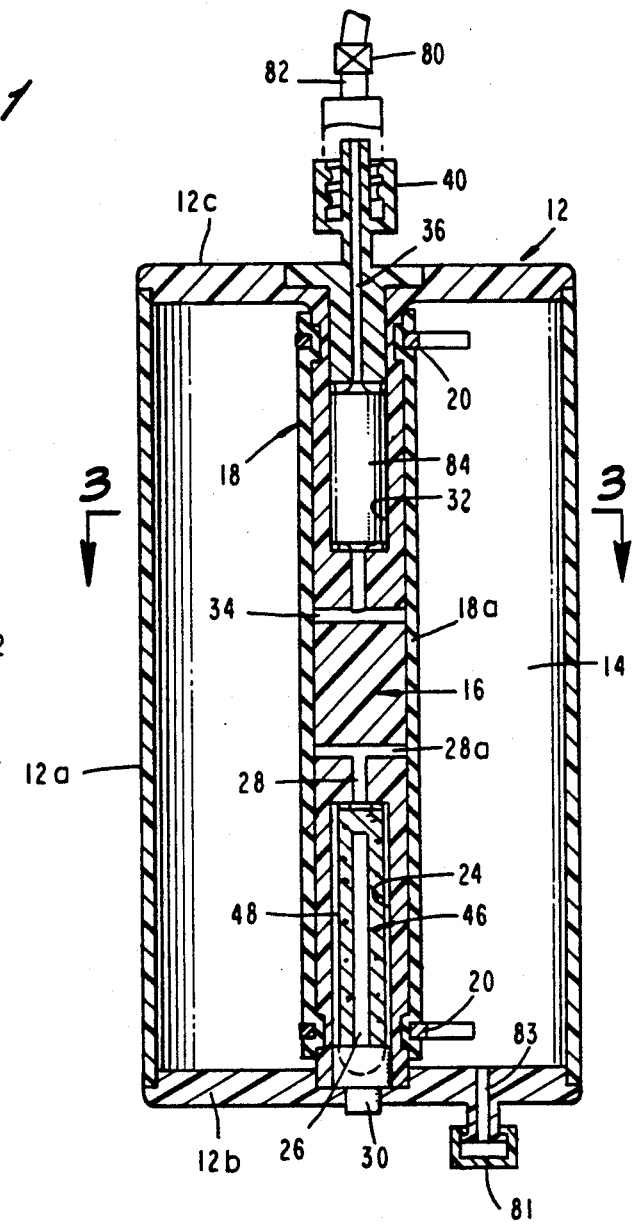
Figure 3:
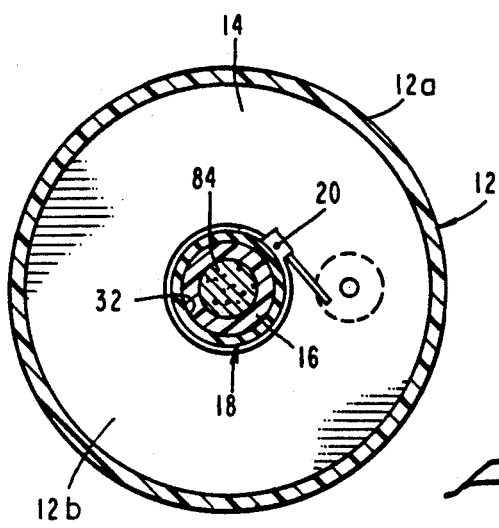
FIG. 3 is a cross-sectional view taken along lines 3—3 of FIG. 2.
Figure 9:
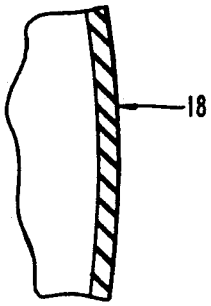
FIG. 9 is an enlarged, cross-sectional view of the area designated by the numeral 9 in FIG. 4.
Figure 10:
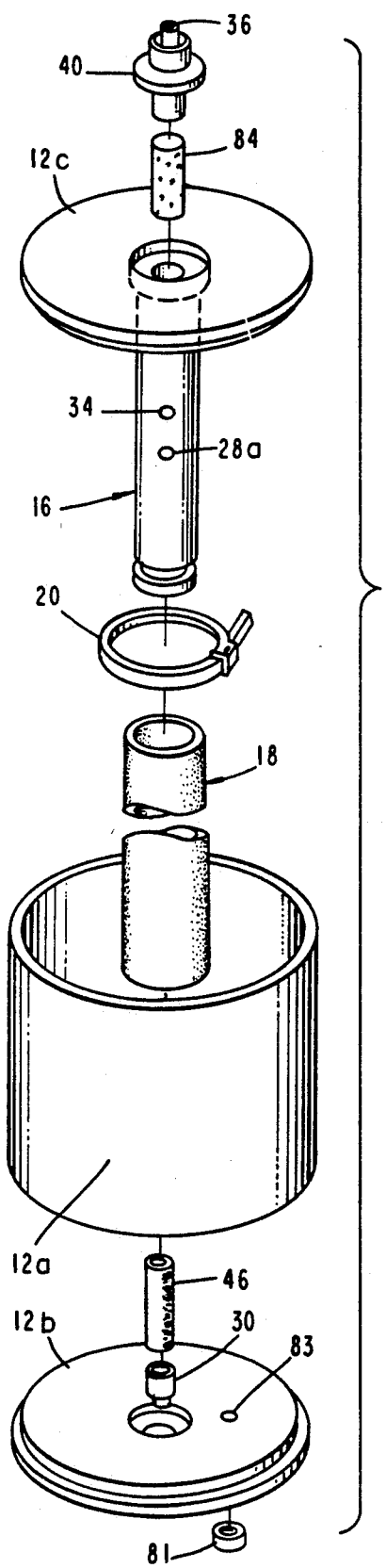
FIG. 10 is a generally perspective exploded view of the fluid dispensing device of this form of the invention.

Referring to the drawings and particularly to FIGS. 1, 2, and 10, the fluid dispenser of one form of the invention can be seen to comprise an elongated housing 12 having an internal chamber 14, a support 16 disposed within internal chamber 14 and extending longitudinally of the housing 12, and a generally cylindrically shaped, elongated elastomeric member 18.

Housing 12 comprises a cylindrically shaped central portion 12a and inlet and outlet end plates 12b and 12c respectively. Central section 12a and end plates 12b and 12c may be constructed of any suitable rigid plastic material such as a polycarbonate and end plates 12b and 12c can be affixed to the central section by any suitable means such as adhesive bonding or an appropriate sonic weldment. Elastomeric member 18 is securely affixed proximate its ends to support 16 by means of suitable ring clamps 20 such as self-locking plastic panduit strips.

As best seen by referring to FIG. 2, support 16 is provided with a first chamber 24 having a fluid inlet 26 and a fluid outlet 28. Fluid inlet 26 is accessible via closure means here shown as a site injection septum 30. Septum 30 can be constructed from a self-sealing, non-coring material such as silicone-SEBS, which can be sealably punctured by a needle of a conventional syringe or may be provided with a slit adapted to accept a blunt cannula of a character well known to those skilled in the art. Septum 30 is receivable within one end of the chamber 24 and extends through end wall 12b of housing 12 in the manner shown in FIG. 2.

Support 16 is also provided with a second chamber 32 having an inlet fluid passageway 34 and an outlet fluid passageway 36. A fluid dispensing means shown here as a luer connector 40 is provided at the outlet end of support 16 in the manner shown in FIG. 2.

It is to be observed that elastomeric member 18 includes a central portion generally designated at 18a which overlays fluid outlet passageway 28 and fluid inlet passageway 34 of support 18.

As previously mentioned, the dispensing device of the present invention is unique in that it provides an opportunity to add to the diluent or other parenteral fluid being introduced into the device via septum 30 selected elements, chemical compounds and biologically active materials such as drugs, medicaments, biological agents and other therapeutic agents (additives). This addition is accomplished by removably affixing selecting additives to various forms of support structures which can be placed into chamber 24 of support member 16 so that they reside within the path of the fluid flowing through inlet fluid passageway 26 and outlet passageway 28 of support member 18.

Before considering the highly important adding means of the invention a brief introductory background is perhaps helpful.

In the past it has been common practice to mix various types of separately packaged drugs with a suitable diluent immediately before they are delivered intravenously to a patent. Typically the drugs are packaged separately from the diluent for various reasons. For example, many drugs do not retain their chemical and physical stability when mixed with a diluent and thus cannot be stored for any substantial period of time. Also, drugs are often packaged separately from the diluent because many firms which manufacture drugs are not engaged in the business of providing medical solutions in containers for intravenous delivery and vice versa.

Traditionally, the mixing of the drug and the diluent was accomplished by a doctor, nurse or medical professional injecting the injectable fluid into a glass vial containing the drug. After mixing the drug and the diluent, the solution thus formed is withdrawn into a syringe barrel and in some instances injected immediately into the intravenous system of a patient. More typically however, the reconstituted drug is injected from the syringes into a larger container of solution for connection to a intravenous administration set. This prior art procedure is time consuming, imprecise and generally undesirable.

The device of this latest form of the invention elegantly overcomes the drawbacks of the prior art reconstituting and delivery techniques by providing in conjunction with the basic fluid delivery device of the invention a simple and precise means for automatically mixing the desired drug with the appropriate diluent at the time the device is filled.

In the paragraphs which follow, wherein the details of this unique reconstitution process will be discussed, the following terms will have the following means:

Element—any of the fundamental substances that consist of atoms of only one kind and that singly or in combination constitute all matter.

Additive—the element, compound, substance, agent, biologically active material, or other material which is to be added to the fluid introduced into the device of the invention.

Parenteral Fluid—any solution which may be delivered to a patient other than by way of the intestines, including water, saline solutions, alkalizing solutions, dextrose solutions, acidifying solutions, electrolyte solutions, reagents, solvents and like aqueous solutions.

Beneficial—Agents any drug, medicament, pharmaceutical, medical polymer, enzyme, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amio acids, carbohydrates, lipids, nucleic acids, proteins, and other biochemicals and substances which may complex or interact with biochemical compounds), such biochemical compounds biologically functioning as . antibodies, antigenic substances, enzymes, co-factors, inhibitors, lectins, hormones, hormone producing cells, receptors, coagulation factors, anti-fungal agents, growth enhancers, histones, peptides, vitamins, drugs, cell surface markers and toxins, among others known to those skilled in the art. Of the group of biologically active materials described, proteins are of utmost current interest because of the large molecule genetically engineered bio-pharmaceuticals as those species to be immobilized on the additive carriers hereinafter to be described. A discussion of the use of biomosaic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition site or element holder, with or without some type of intermediate matrix.

Additive Presentation Means—Any means such as a functional support or substrate for presenting the additive to the fluid flowing through the device. The functional substrate can comprise a polymer, copolymer, and inter-polymer, a ceramic, a crystal sponge, a carbon based matrix, a celullosic glass, plastic biomosaic polymers, azlactone-functional polymer beads, adduct beads, carboxylate-functional polymer beads, gums, gels, filaments and like carriers.

Figure 11:
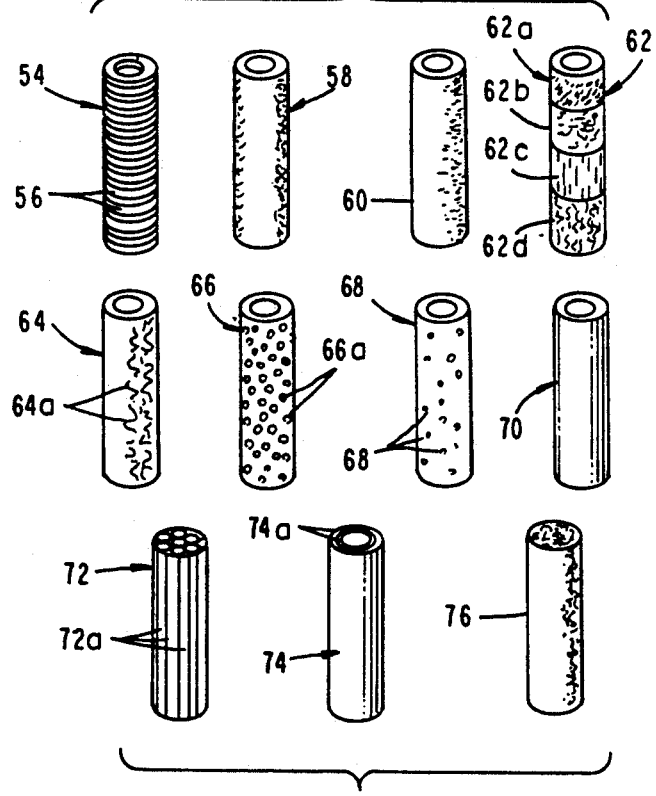
FIG. 11 is a generally perspective view of various forms of the structural support portion of the adding means of the invention for adding an additive to the fluid introduced into the storage reservoir of the device.

The adding means of the invention can take several different forms such as those illustrated in FIG. 11. However, in its preferred form, the adding means comprises a cylindrically shaped, microporous polymeric functional support structure 46 which is disposed within chamber 24 of the support and to which various additives, including beneficial agents such as drugs, biologically active materials, and chemical elements and compounds which can be releasably connected. These additives are carried by the structure in a manner such that, as the liquid, such as a diluent, reagent or other aqueous solvent flows through a central passageway 46a and circulates through the support assembly in the manner shown by the arrows in FIG. 6, the additives will be presented to the liquid flow and efficiently added to the liquid as it flows toward outlet passageway 28 and into the reservoir.

The additives themselves can also take various physical forms including liquid, solid, granular, powder, particle, gel, wax hydrocolloid carriers, such as gum film, tablet, crystalline, emulsions, microcrystalline, microspherical, spray dried compounds and lypohilized compounds and saturants. The additives can be removable connected to, immobilized on, impregnated within or supported by support means in a number of ways. The additives can be chemically or mechanically attached, affixed, or bound directly or indirectly through cooperation with an intermediate matrix. They can be captured, affixed, linked, or cross-linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited suspended or occluded within voids, cells, tubules and intersticies formed in the support. One important method for removably affixing the additive to the functional support means includes treating the functional support means with a compound having reactive functional groups such as a azlactone functional compounds with their high binding capacity. In certain appliations, the biologically active material can be bound at the surfaces of biomosaic polymers in the manner described in EPO Patent No. 0 430 517 A2. Similaraly, graft copolymers can be used in the manner described in U.S.Pat. No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking bioseparation diffusion, washing, disintegration, errosion, disassociation, desorbsion, solubilization, leeching, enzymatic cleavage, biological reaction, osmosis, separated from ring opening materials and like separation means.

Turning now to FIGS. 2 and 6, one form of adding means or additive carrier is there illustrated. This form of the adding means comprises a generally cylindrically shaped porous substrate 46.

In using the apparatus of the invention, septum or non-coring injection site 30 is penetrated by needle 47 of a syringe and a parenteral fluid, such as a sterile diluent, is introduced into inlet passageway 26 using the needle syringe. As indicated by the arrows in FIG. 6 as the diluent flows longitudinally of inlet passageway 26 it will pass through porous member 46, into flow channels 48 which surround substrate 46 (FIG. 7) and then into fluid reservoir 50 (FIG. 4) via outlet passageway 28. Circumferentially spaced flow fins 49 direct the flow through transverse passageways 28a (FIG. 8). This diluent flow under pressure will urge bladder 18 outwardly into the position shown in FIGS. 4 and 5. As the liquid flows through porous functional support member 46, the additives presented to the liquid will be releasably separated from the functional support and added to the flow, or solubilized by the diluent, thereby activating the diluent to form the therapeutic solution to be dispensed to the patient.

The liquid, such as a parenteral fluid, which is introduced into passageway 26 can include, by way of example, a reagent, a sterile diluent, various electrolytes, aqueous solutions or reagents such as aqueous solutions of dextrose, saline solutions, alkalinizing solutions, acidifying solutions, polyonic solutions and any other liquids that can serve as a vehicle for the administration of therapeutic or beneficial agents which are desirable to administer to the patient by infusion.

Turning now to FIG. 11 various other forms of adding means or additive assemblies are there illustrated. For example, numeral 54 identifies an assembly comprising a plurality of annular wafers 56 each of which is coated with the selected additive. The wafers are stacked in the manner shown in the drawing to provide a multiplicity of exposed surfaces and alternatively spaced reaction sites which are exposed to the diluent as it flows through chamber 24. Numeral 58 designates a porous substrate with interconnecting voids, such as a porous ceramic with various coatings containing one or more additives deposited within the voids. The selected additives such as elements, chemical compounds or drugs are contained within the deposited material and are deposited, or immobilized thereon by techniques well known to those skilled in the art. The additives contained within the voids are, of course, presented or exposed and then introduced into the sterile diluent as the diluent flows along passageway 26.

Another form of additive assembly designated in FIG. 11 by the numeral 60 comprises tubular member having a multiplicity of internal, alternate sized pores which are plugged with selected additives such as chemical compounds and beneficial agents, or medicaments.

Another slightly more complex additive assembly is identified by the numeral 62. This assembly is made up of a plurality of spaced apart, porous disk shaped wafers 62a, 62b, 62c and 62d each wafer being of the same or different construction and porosity and each having a multiplicity of reactive sites presenting to the liquid flow specially selected individual species of additives such as beneficial agents, elements or compounds so that multiple reactivities and selectivities can be achieved. With this construction, a wide variety of liquid flow rates, and complex sequential separations and priority staged substance introduction into the system reservoir can be achieved by specially designing each of the wafers having unique affinity and separation characteristics that cooperate to make up the function structural support.

The numeral 64 of FIG. 11 identifies yet another form of the additive means of the invention. In this form of the invention, a generally cylindrically shaped functional support means is formed from a multiplicity of microporous polymers 64a presenting a multiplicity of reactive sites.

Still another form of the additive assembly is identified by FIG. 11 by the numeral 66. This assembly comprises a cylindrical, porous plug like member made up of a multiplicity of fused together microspheres 66a each of which is coated with a separation or reactive coating upon which is deposited an additive such as a biologically active material or other beneficial agent.

The additive assembly designated in FIG. 11 by the numeral 68 is made up of a high porosity, semi-synthetic celullosics 68a formed into a generally cylindrical shape and having interconnecting intestial surfaces and voids or functional support means and is similar in size and configuration to activating assembly 46.

Additive assembly 70 comprises a cylindrically shaped porous structure which is provided with pores of varying sizes only some of which are coated, plugged or impregnated with selected additives and as necessary functions, intermediate materials.

The additive assembly 72 of FIG. 11 comprises a cylindrically shaped structure made up of a plurality of interconnected bundles 72a the exposed surfaces of which carry the selected additive which has been removably interconnected thereto as a coating, vapor deposition or other chemical attachment.

Another form of adding means is identified in FIG. 11 by the numeral 74. Here the adding means is provided as a cylindrical structure formed from a plurality of coating, cladding, emulsion or deposition layers 74a or laminated around a porous core.

Finally, the functional support member identified in FIG. 11 by the numeral 76 exemplifies yet another form of adding means of the invention. This member, which is also of a generally cylindrically shaped configuration is constructed from a porous ceramic material into which selective additives and intermediate matrix compounds have been removably affixed.

Assemblies 54 through 76 which may be soluble or insoluble are intended to merely exemplify, not to limit, the wide variety of materials, constructions and techniques for affinity and separation that can be used to introduce the desired additives into the liquid flow introduced into the inlet flow passageway 26 of the device.

After the diluent or other parenteral fluid is introduced into the device and mixed with the additive, the solution has formed closure means such as a valve or clamp 80 provided on infusion line 82 is opened (FIG. 2). When valve 80 and venting port 83 are opened, the bladder 18, within which internal stresses have been imparted by the fluid flowing into the device via passageways to its less distended initial starting position urging fluid through passageway 34. Port 83 is normally closed by a removable cap 81. The fluid, which is now the diluent mixed with the additive, flow into chamber 32 and through flow rate control means shown here as a porous rate control filter 84. Filter 84 can be constructed from a porous ceramic or other suitable porous plastic material such as polysulfone and can be provided with the desired porosity in a manner well known to those skilled in the art.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid dispensing device comprising:
   (a) an elongate housing having walls defining an internal chamber;
   (b) a support connected to said housing, said support having:
      (i) a first chamber having a fluid inlet and a
      (ii) a fluid passageway having a fluid inlet and a fluid outlet;
      (iii) filling means for introducing fluid into said fluid inlet of said first chamber; and
      (iv) dispensing means in communication with said fluid outlet of said fluid passageway for dispensing fluid from said dispenser;
   (c) an elongate tubular shaped elastomeric member connected proximate its ends to said support, said elastomeric member having a central portion disposed within said internal chamber of said housing and overlaying said fluid outlet of said first chamber and said fluid inlet of said fluid passageway, said central portion of said elastomeric member being distendable by fluid flowing through said fluid outlet of said first chamber from a first position in proximity with said support to a second position; and
   (d) adding means contained within said first chamber of said support for adding an additive to fluid flowing through said fluid inlet of said first chamber.

2. A device as defined in claim 1 in which said adding means comprises a member having an exposed region, said additive being present at said region, said member being disposed within said first chamber of said support to that said additive will be added to said fluid flowing into said first chamber via said inlet thereof.

3. A device as defined in claim 1 in which said adding means comprises a member disposed within said first chamber of said support, said member having exposed surfaces and a beneficial agent removably affixed to said exposed surfaces.

4. A device as defined in claim 1 in which said adding means comprises a member disposed within said first chamber of said support, said member having exposed surfaces and a drug present on said exposed surface.

5. A device as defined in claim 1 in which said housing comprises a cylindrical body having first and second end plates, said support extending between said end plates.

6. A device as defined in claim 1 in which said housing is vented to atmosphere.

7. A device as defined in claim 1 further including fluid flow rate control means disposed within said fluid passageway of said support.

8. A device as defined in claim 1 in which said support further includes a second chamber in communication with said fluid passageway, said fluid flow control means comprising a porous member disposed within said second chamber.

9. A fluid dispensing device comprising:
   (a) an elongate housing having first and second ends and walls defining an internal chamber;
   (b) an elongate generally cylindrically shaped support connected to said ends of said housing, said support having:
      (i) a first fluid passageway having an inlet and an outlet;
      (ii) a second fluid passageway having an inlet and an outlet;
      (iii) filling means for introducing fluid into said inlet of said first fluid passageway; and
      (iv) dispensing means in communication with said fluid outlet of said second fluid passageway for dispensing fluid from said dispenser;
   (c) an elongate tubular shaped elastomeric member connected proximate its ends to said support, said elastomeric member having a central portion disposed within said internal chamber of said housing and overlaying said fluid outlet of said first fluid passageway and said fluid inlet of said second fluid passageway, said central portion of said elastomeric member being distendable by fluid flowing through said fluid outlet of said first fluid passageway from a first position in proximity with said support to a second position; and
   (d) adding means disposed within said first fluid passageway for adding an additive to fluid flowing through said first fluid passageway.

10. A device as defined in claim 9 in which said adding means comprises a substrate disposed within said first fluid passageway and said additive comprises a beneficial agent removably carried by said substrate.

11. A device as defined in claim 10 in which said substrate comprises a generally cylindrically shaped porous member having a multiplicity of interconnected, interstitial pores, said beneficial agent being disposed within said pores.

12. A device as defined in claim 10 in which said substrate comprises a plurality of annular shaped wafers, said beneficial agent being coated on said wafers.

13. A device as defined in claim 10 in which said beneficial agent comprises a biologically active material.

14. A device as defined in claim 10 in which said beneficial agent comprises a drug.

15. A fluid dispensing device comprising:
   (a) an elongate housing including a generally cylindrically shaped center portion having interior walls defining a chamber and first and second plates connected to said center portion;
   (b) an elongate generally cylindrically shaped support connected to said end plates and extending longitudinally of said center portion, said support having:
      (i) a first chamber having a fluid inlet and a fluid outlet;
      (ii) a second fluid chamber having a fluid inlet and a fluid outlet;
      (iii) filling means for introducing fluid into said inlet of said first chamber; and
      (iv) dispensing means in communication with said fluid outlet of said second chamber for dispensing fluid from said dispenser.
   (c) fluid flow rate control means disposed within said second chamber for controlling the rate of flow of fluid therethrough;
   (d) an elongate tubular shaped elastomeric member connected proximate its ends to said support, said elastomeric member having a central portion disposed within said internal chamber of said housing and overlaying said fluid outlet of said first chamber and said fluid inlet of said fluid passageway, said central portion of said elastomeric member being distendable by fluid flowing through said fluid outlet of said first chamber from a first position in proximity with said support to a second position; and
   (e) adding means disposed within said first chamber for adding an additive to fluid flowing through said first fluid passageway, said adding means comprising a tubular shaped substrate disposed within said first chamber said additive being carried by said substrate for presentation to fluid flowing through said first chamber.

16. A device as defined in claim 15 in which said additive comprises a beneficial agent removably connected to said substrate.

17. A device as defined in claim 16 in which said dispensing means comprises a luer connector.

18. A device as defined in claim 17 in which said housing includes venting means for venting said chamber of said housing.

* * * * *